United States Patent [19]

Unruh

[11] 4,152,344

[45] May 1, 1979

[54] PHOSPHINO-FERROCENE LIGANDS

[75] Inventor: Jerry D. Unruh, Corpus Christi, Tex.

[73] Assignee: Celanese Corporation, New York, N.Y.

[21] Appl. No.: 822,859

[22] Filed: Aug. 8, 1977

[51] Int. Cl.² ............................................. C07F 17/02
[52] U.S. Cl. ........................ 260/439 CY; 260/604 HF
[58] Field of Search ................ 260/604 HF, 439 CY; 252/431 P

[56] References Cited

PUBLICATIONS

Bishop et al., J. Organometal Chem., 27 241 & 244 (1971).
Chemical Abstracts 63, 18147b-d (1965).
Chemical Abstracts 58, 11398b (1963).
Evans et al., J. of Chem. Soc. A, pp. 3133-3142, (1968).
Knifton, J. Org. Chem. 41, No. 17, pp. 2885-2890, (1976).
Pruett, J. Org. Chem. 34 No. 2, pp. 227-330, (1969).
Tanaka et al., Bull. of the Chem. Soc. of Japan, vol. 50 (9) pp. 2351-2357, (1977).

*Primary Examiner*—Helen M. S. Sneed
*Attorney, Agent, or Firm*—Ralph M. Pritchett

[57] ABSTRACT

An improved process for hydroformylating an ethylenically-unsaturated compound to form an aldehyde derivative thereof in the presence of rhodium hydridocarbonyl in complex combination with an organic ligand, characterized by employing as said organic ligand a compound having two phosphino moieties, one being of the formula:

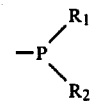

and the other being of the formula:

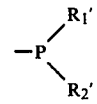

wherein $R_1$, $R_2$, $R_1'$, and $R_2'$ are organic radicals at least one of which contains an electronegative substituent moiety. The presence of the electronegative substituent in the ligand leads to an increased ratio of linear aldehyde to branched-chain aldehyde in the hydroformylation reaction product.

3 Claims, No Drawings

PHOSPHINO-FERROCENE LIGANDS

BACKGROUND OF THE INVENTION

Processes for preparing carbonyl compounds, e.g., aldehydes by hydroformylating an ethylenically-unsaturated precursor in the presence of a catalyst comprising rhodium hydridocarbonyl in complex combination with an organic ligand are well-known in the art and are now coming to be of increasing industrial importance. Typical of such processes is the hydroformylation of propylene to form butyraldehyde. These rhodium-based processes are now favored over the older technology wherein cobalt carbonyl is the major catalyst component for several reasons, including the fact that the rhodium systems can be used under relatively mild reaction conditions. Also, of very great importance, the rhodium-catalyzed systems can be controlled so as to yield a product in which the normal isomer of the aldehyde predominates over the branched-chain isomer to a greater extent than has normally been obtainable heretofore with the older reaction systems. It is to be understood that for most industrial purposes the normal aldehyde is strongly preferred over the branched-chain isomer as in, for example, those systems in which an aldehyde is initially formed, as by hydroformylation, and then oxidized to form the corresponding carboxylic acid which is then used as an intermediate in the production of synthetic lubricant base stocks. Considering heptaldehyde, for example, this compound is of very great importance as an intermediate in the production of heptanoic acid, certain esters of which are excellent base stocks for synthetic lubricant formulation, whereas the corresponding branched-chain acid is much less useful for this purpose.

More recently it has been discovered, as disclosed in Belgian Pat. No. 840906 (Oct. 20, 1976) and British Pat. No. 1,402,832, that bidentate ligands are particularly useful, with Belgian Pat. No. 840906 in particular disclosing that certain bidentate ligands which are derivatives of ferrocene are capable of yielding, under very moderate hydroformylation reaction conditions, an unusually high ratio of normal isomer to branched-chain isomer in the aldehyde product without the necessity of employing a high ratio of ligand to rhodium in the catalyst. More specifically, Belgian Pat. No. 840906 discloses that, with the ferrocene-based ligands, including specifically diphosphino-substituted ferrocenes, there is little need for maintaining in the reaction zone more than about 1.5 moles of the ferrocene derivative per atom of rhodium (equivalent to a phosphorus:rhodium mole ratio of 3.0:1). More recently yet it has been discovered, as set forth in U.S. Patent application Ser. No. 783,121 filed on Mar. 31, 1977 by J. D. Unruh and L. E. Wade, that there is another family of bidentate hydroformylation ligands which gives commercially attractive results similar to those of the ferrocene-based ligands, these newer ligands comprising cyclic compounds having in the ring two adjacent phosphinomethyl-substituted carbon atoms which are in trans relationship to one another and between which the dihedral angle of the trans positions is from about 90° to about 180°.

In view of the foregoing it can be seen that bidentate ligands, and particularly diphosphino ligands, have come to be recognized as an advance over the relatively simple ligands, normally monodentate, which until recently have been considered typical and entirely satisfactory.

The industry continues, however, to seek further improvement in these rhodium-complex hydroformylation catalyst systems for several reasons which include (a) the recognition that any measures for reducing reaction pressure and temperature without suffering a loss in reaction conversion rate and normal:isoaldehyde ratio in the product will greatly reduce operating cost and (b) rhodium and the ligands both being costly, anything to improve catalyst efficacy and catalyst longevity will reduce both operating costs and investment cost. It is also to be kept in mind, of course, that the supply of rhodium available throughout the world is limited, so that obtaining maximum productivity per unit amount of rhodium-based catalyst is in itself a matter of unusual importance.

It is, accordingly, an object of the present invention to provide an improved hydroformylation process employing catalysts comprising rhodium hydridocarbonyl in complex combination with bidentate organic ligands, in particular diphosphino ligands. It is a further object to provide new ligands for use in such rhodium-catalyzed hydroformylation processes, the use of which facilitates operation at lower catalyst concentrations than are required with prior-art ligands. It is a further object to provide a method of general applicability for improving the efficacy of a given ligand by incorporating into its molecule certain substituent moieties which it has now been found have the effect of improving its efficacy in hydroformylation reaction systems.

Other objects will be apparent from the following detailed specification.

SUMMARY OF THE INVENTION

In accordance with the present invention, an ethylenically-unsaturated compound, e.g., an alkane, is hydorformylated to form an aledhyde derivative thereof by reaction with a carbon monoxide-hydrogen synthesis gas in the presence of a liquid reaction medium which contains, as the hydroformylation catalyst, rhodium hydridocarbonyl in complex combination with an additional organic ligand which is a compound having two phosphino moieties, one being of the formula:

and the other being of the formula:

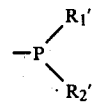

wherein $R_1$, $R_2$, $R_1'$, and $R_2'$ are organic radicals at least one of which contains an electronegative substituent moiety. It is strongly preferred that there be maintained in the liquid reaction medium contained in the hydroformylation reaction solvent at least about 1.5 moles of the ligand per atom of rhodium. That is, the ratio of phosphorus atoms to rhodium atoms in the catalytic complex should be at least about 3.0:1.0.

It will be understood that carbon monoxide and hydrogen are themselves ligands in the present catalyst systems, but the term "ligand" or "additional organic ligand" will be used hereinbelow to designate the ligands which are employed in addition to carbon monoxide and hydrogen to make up the improved catalyst systems to which the present invention is directed.

The heart of the invention lies in the use of the electronegative moiety-substituted "R" groups in the ligand, with maintenance of the phosphorus:rhodium ratio of at least 3:1 also being very important in operating the process at maximum effectiveness. By using the present improved ligands in the presently-recommended ratio of ligand to rhodium, the hydroformylation reaction yields a product which contains normal and branched-chain aldehyde derivatives of the olefinic feedstock in which the ratio of normal to branched-chain aldehyde is surprisingly higher than would be obtained, under otherwise-identical reaction conditions of pressure, catalyst concentration, etc. when using as the catalyst any of the prior-art catalysts even including the improved bidentate ligands as described in, for example, Belgian Pat. No. 840906 and British Pat. No. 1,402,832 previously discussed hereinabove.

It will be recognized that employment of the present improved catalyst complexes does not require a knowledge of the exact manner in which the rhodium is incorporated into the complete catalytically active complex. Broadly, it is known that the rhodium is in complex combination with ligands comprising carbon monoxide and an additional organic ligand. More specifically the catalytically-active complex is considered to be rhodium hydridocarbonyl in complex combination with an additional ligand (i.e., the improved ligands which are central to the present invention), but the present invention does not reside in any particular theory as to how the rhodium complex is structured.

Aside from the employment of the present improved catalyst system, the reaction conditions which are used in the present process are those of prior art as already generally understood, although it is not necessary to employ catalyst concentrations as high as normally used in the prior art.

DETAILED DESCRIPTION OF THE INVENTION

The parent ligands, by which is meant the ligands the performance of which is improved by incorporating into them the electronegative substituents of the present invention, include broadly all of the already-known hydroformylation ligands which have at least two phosphino groups as represented broadly by the formula:

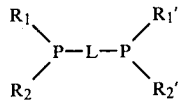

wherein $R_1$, $R_2$, $R_1'$, and $R_2'$ are organic, normally hydrocarbyl, groups and wherein L is an organic moiety which may be substituted and which may be an organo metallic compound as exemplified by ferrocene. More than two of the phosphino groups can be present (i.e., the ligand can be tridentate or tetradentate, for example) although as a practical matter there will be only two phosphino moieties. To recapitulate, any known polyphosphino ligand will be improved in its efficacy by the incorporation of the present electronegative substituent groups, but diphosphino ligands are of particular industrial importance for the present purposes. Likewise, arsenic or antimony analogs of the phosphino-based ligands can also be employed, although here again the phosphino ligands are of particular industrial importance so that the present improvements are directed primarily to them. Particularly useful parent ligands include, however, compounds in which L is either (a) ferrocene (to which the dihydrocarbylphosphino substituents are to be attached in the 1 and 1' positions) and (b) cyclic compounds which have in the ring two adjacent carbon atoms each of which is attached to a methylene group (one of the two phosphino moieties then being attached to each of these methylene groups). The latter category is particularly efficacious in hydroformylation processes when said two adjacent ring carbon atoms have, between their trans positions (to which said methylene groups are attached), minimum and maximum attainable dihedral angles which are, respectively, not less than about 90° and not more than 180°. It is to be understood, however, as explained above, that L can be any organic moiety, substituted or unsubstituted, the diphosphino derivatives of which are known in the existing art to be useable as ligands in rhodium-catalyzed hydroformylation processes.

$R_1$, $R_2$, $R_1'$, and $R_2'$ can be alike or different, although as a practical matter they will ordinarily be alike since the synthesis of ligands in which these groups are different from one another is comparatively difficult and the use of mixed phosphino substituents provides no additional advantage. Normally $R_1$, $R_2$, $R_1'$ and $R_2'$ are hydrocarbyl groups, perferably of from 1 to about 20, especially from 1 to about 12 carbon atoms. They may be alkyl, aryl, cycloalkyl, aralkyl or alkaryl, but phenyl groups are specifically useful and the precursor compounds required for synthesizing the bis(diphenylphosphino) ligands are readily available. Alternatively, $R_1$, $R_2$, $R_1'$, and $R_2'$ can be simple alkyl groups, especially of from about 1 to about 12 carbon atoms, precursor compounds for synthesizing phosphino moieties containing such lower alkyl groups being also available.

The electro-withdrawing moieties which are to be attached to the hydrocarbyl groups attached to the phosphorus atoms in the ligands are, broadly, all those moieties which are characterized by having a positive Hammett's sigma value as explained in Gilliom, R. D., *Introduction to Physical Organic Chemistry*, Addison-Wesley, 1970, Chapter 9, pp. 144–171. The higher the sigma value, the more efficacious the substituent moiety will be when employed in the present improved process. The substituent should be attached to the hydrocarbyl group at a position such that it (the substituent moiety) will be separated from the phosphino phosphorus atom by not more than about six carbon atoms. When the hydrocarbyl radical is aryl, as exemplified by the phenyl radical which is particularly suitable for the present purposes, the substituent moiety should be in the meta or the para position except, however, that, when the substituted hydrocarbyl radical is phenyl and the substituent moiety is an alkoxy or hydroxyl group, then the substituent should be attached only at the meta position. (This is consistent with the requirement set forth above that the Hammett sigma value be positive in all cases, since alkoxy and hydroxyl moieties in the para position actually have a negative Hammett sigma value.) Acetylamino and phenyl groups are also negative in the para position, but as a practical matter these substituents are not likely to be encountered.

While it is to be understood that, as already explained, any substituent moiety having a positive Hammett sigma value can be used, the following substituent moieties are specifically illustrative: meta-fluoro; para-fluoro; para-trifluoromethyl; meta-trifluoromethyl; di-meta-trifluoromethyl; para-chloro; meta-chloro; para-bromo; meta-bromo; para-nitro (but only with exercise of caution in preparing and storing); para-cyano; and meta-methoxy (but not para-methoxy, as explained above), ethoxycarbonyl, acetoxy, acetyl, acetylthio, methylsulfonyl; methylsulfanyl, sulfamoyl, and carboxy.

The benefits of inserting the above-described substituent moieties into the hydrocarbyl (or, more broadly, organic) groups which are attached to the phosphino phosphorus atoms to some extent when even one of the four R groups is so substituted. The beneficial effect is additive, however (although not necessarily linear), so that it is preferred that all four R groups have the electronegative substituents. Commonly, $R_1$, $R_2$, $R_1'$, and $R_2'$ will all be identical and each of these groups will also have the same electronegative substituents attached to it. This is not essential, however, the use of mixed R groups having also mixed electronegative substituents not being excluded.

When the hydrocarbyl group attached to the phosphorus atoms is alkyl instead of phenyl or other aromatic moiety, the same halo, haloalkyl, nitro, cyano, alkoxy, etc. electronegative substituents listed above can also be employed although, of course, the terms "meta" and "para" would not apply. In such cases, as previously explained, the electronegative substituent should be at such a position on the hydrocarbyl moiety that it is separated from the phosphino phosphorus atom by not more than about 6 carbon atoms, preferably 1 to 4 carbon atoms.

While many alternatives and/or modifications will suggest themselves to those skilled in the art, the preparation of the electronegatively-substituted diphsophino ferrocene ligands for use in the present improved process may be outlined as follows:

One begins with the Grignard reagent corresponding to the electronegative-substituted moiety it is desired to incorporate into the substituted ligand which is ultimately to be synthesized. That is, for example, when it is desired that the electronegative-substituted "R" in the final ligand product is to be 4-trifluoromethylphenyl, one begins with the Grignard reagent which is made from 4-trifluoromethylbromobenzene. The Grignard reagent is then reacted with $(CH_3CH_2)_2NPCl_2$ (diethylaminodichlorophosphine) to form

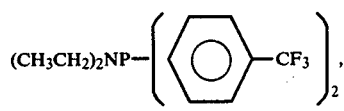

which is then treated with anhydrous HCl to form bis(4-trifluoromethylphenyl)phosphinous chloride. The synthesis up to this point is discussed in greater detail by K. S. Yudina, T. Y. Medved, M. I. Kabachnik, *Izv. Akad Nauk, SSSR*, Ser. Khim, 1954–58 (1966). Chem. Abstr., 66, 7609u (1967), and K. Issleib and W. Seidel, Chem. Ber. 92, 2681–94 (1959).

An adduct of tetramethylethylenediamine and n-butyl lithium is then formed in a suitable inert liquid, e.g., n-hexane, after which the adduct in the inert liquid is then slowly added to a solution of ferrocene in, preferably, the same inert liquid, i.e., n-hexane. Following this, the bis(4-trifluoromethylphenyl)-phosphinous chloride is then slowly admixed into the mixture of ferrocene and adduct the preparation of which has just been described, to form the desired electronegatively-substituted ligand, which is a yellow-brown solid. A small amount of water is added to destroy any excess butyl lithium or chlorophosphine which may be present, and the solid adduct is then filtered out and washed with water and with liquid hexene. It is then dried, advantageously in a current of air at about ambient temperature and/or in a vacuum chamber. This portion of the synthesis is analogous to the snythesis described by Bishop et al. in Bishop, J. J., et al., *J. Organometal Chem*, 27, 241 (1971).

To prepare the electronegatively-substituted ligands discussed herein other than those based on ferrocene, one also begins with the Grignard reagent as discussed hereinabove and follows the same procedures down through and including the separation of the, for example, bis(4-trifluoromethylphenyl)phosphinous chloride. After this, however, the next step with this latter group of ligands is to react the bis(4-trifluoromethylphenyl)-phosphinous chloride with metallic sodium in a dry mixture of dioxane and tetrahydrofuran to form the corresponding sodium phosphide. This is discussed more fully in Houben-Weyl "Methoden Der Organische Chemie", Volume 12/1, pp. 23–24. The phosphide is then reacted with the ditosylate corresponding to the desired ligand by methods which are described more fully in British Pat. No. 1452196 (Rhone-Poulenc) and the more detailed literature sources which are identified in that patent. British 1452196 presents a particularly useful discussion of the synthesis of ligands having two phosphino moieties attached to cyclic structures, with the exception that it does not disclose the present improvement which lies in the incorporation of the electronegatively-substituted moiety into the diphosphino ligands.

Incorporating the ligand into the complete catalytic complex comprising the ligand and rhodium hydridocarbonyl can be carried out by methods already known to the art as exemplified, for example, by the disclosure of Belgian Pat. No. 840906 issued Oct. 20, 1976. Advantageously, for example, a rhodium compound containing carbonyl moiety in the molecule—as exemplified by rhodium carbonyl itself—is simply mixed with the ligand in a suitable inert liquid, which conveniently can be the solvent which is to be used in the subsequent hydroformylation reaction itself (e.g., toluene or a liquid alkane or any of the many known hydroformylation reaction solvents including liquids comprising predominantly the hydrocarbon reactants and/or the hydroformylation reaction products themselves, which are usable as hydroformylation liquid reaction media even though they are not, strictly speaking, chemically inert). The resulting mixture of ligand and rhodium carbonyl can then simply be injected directly into the hydroformylation reaction zone, where, in the presence of hydrogen:carbon monoxide synthesis gas and under the conditions of pressure and temperature normally obtained in hydroformylation reaction systems, the formation of the desired catalytic complex is completed.

Another useful rhodium source in forming the catalytic complex is the complex hydrocarbonyltris(triphenylphosphine)rhodium(I) or $HRh(CO)(P\phi_3)_3$. This is itself, of course, a complex of rhodium hydridocarbonyl with a ligand (triphenylphosphine). To be industrially attractive in hydroformylation reactions, however, it must be used with a substantial excess of the triphenylphosphine (i.e., substantially more than a 3:1 ratio of triphenylphosphine to rhodium) by simply using this complex as the rhodium source, however, in an improved complex wherein the present improved ligand is also added, one obtains a greatly improved catalyst in which the triphenylphosphine moiety is only a diluent which contributes little if anything to the efficacy of the mixture. Other sources of rhodium will also suggest themselves to one skilled in the art and are discussed further hereinbelow.

As just explained, the complex is formed by introducing the ligand and the rhodium source, along with a chloride scavenger if one is called for, into the hydroformylation reaction zone wherein, under the conditions obtaining therein, the catalytically active complex is formed in the presence of the synthesis gas. Enough ligand should be employed that the resulting mixture of ligand and rhodium contains at least about 3.0 phosphino moieties per atom of rhodium. A lower phosphorus:rhodium ratio results in reduced catalytic effectiveness, but these ligands are quite effective at phosphorus:rhodium ratios as low as 3.0:1. That is, there is a very definite increase in catalytic effectiveness of each of these ligands as the phosphorus:rhodium ratio is increased up to 3.0:1; the effect of further increases in the ratio is less pronounced. It is, of course, always desirable to maintain a phosphorus:rhodium ratio at least slightly above 3:1 in order to be sure that the ratio does not inadvertently fall below this desired level as a result of, for example, metering errors that might occur in the course of adding rhodium and ligand to a reactor especially at low flow rates.

As is already well understood in the existing art, the hydroformylation of an olefinic feedstock, e.g., an alkene, by processes of the present type is effected by introducing into a reaction zone contained in a reaction vessel of coventional type the olefin to be hydroformylated (in either gas or liquid form) along with a gaseous mixture of hydrogen and carbon monoxide. The reaction vessel contains a liquid reaction medium in accordance with the well-known technology of hydroformylation chemistry as further discussed hereinbelow, and the catalytic complex is dissolved or suspended in this liquid reaction medium. Toluene exemplifies the usual inert solvents or reaction media used in these systems, but many other liquids can be employed, such as benzene, xylene, diphenyl ether, alkanes, aldehydes and esters, the aldehydes and esters often conveniently comprising products and/or byproducts of the hydroformylation reaction itself. Selection of the solvent is outside the scope of the present invention, which is drawn more particularly to improving the catalysts for these reaction systems rather than to other modifications of the system itself. In the reaction zone the catalytic complex serves to catlyze the hydroformylation of the olefin with the hydrogen and the carbon monoxide to form a mixture of aldehydes containing one more carbon atom than the olefin reactant. Typically, it is desired to employ a terminally-unsaturated olefin, and it is normally preferred that the terminal carbon atom be the site of attachment of the carbonyl group which is introduced by the hydroformylation reaction. The nature of the catalyst employed affects this matter of whether a normal aldehyde is produced (i.e., whether the terminal carbon atom of the olefin is the site of hydrocarbonylation as compared with the second carbon atom in the chain), and the present improved ligands impart very desirable properties to the hydroformylation catalyst in this regard. That is, they produce a high proportion of aldehyde product in which the terminal carbon atom has been carbonylated.

The olefinically-unsaturated feedstock which is to be hydroformyulated by the present improved process can be any of the many types of olefin already known in the art to be suitable for rhodium-catalyzed hydroformylations, especially olefinic compounds having in the molecule up to about 25 carbon atoms. Although mono-unsaturated compounds are normally employed and of particular practical importance, di- and tri-ethylenically unsaturated olefins can also be used, the product in each case being, if complete hydroformylation is carried out, a derivative having up to one additional carbon atom for each ethylene double bond in the parent compound. Olefinic compounds having substituted groups, e.g., ethyenically-unsaturated alcohols, aldehydes, ketones, esters, carboxylic acids, acetals, ketals, nitriles, amines, etc. can be easily hydroformylated as well as the simple mono-alkenes which are particularly useful and of particular commercial importance. Broadly, ethylenically-unsaturated compounds which are free of atoms other than carbon, hydrogen, oxygen, and nitrogen are readily hydroformylated, and more particularly compounds consisting solely of oxygen, hydrogen, and carbon. Some specific classes of substituted olefins to which the hydroformylation process is applicable are: unsaturated aldehydes such as acrolein and crotonaldehyde; alkanoic acids such as acrylic acid; and unsaturated acetals, such as acrolein acetal. More commonly, suitable hydroformylation feedstocks include the simple alkenes such as ethylene, propylene, the butylenes, etc.; alkadienes such as butadiene and 1,5-hexadiene; and the aryl, alkaryl, and aralkyl derivatives of the foregoing. Lower mono-alkenes of 2 to about 12 carbon atoms are especially useful. Hydroformylation does not normally take place within the benzene ring of olefins having aryl substitution, of course, but rather in the ethylenicallyunsaturated portion of the molecule.

Process operating parameters to be employed in practicing the present process will vary depend upon the nature of the end product desired, since, as already known in the art, variation of operating conditions can result in some variation in the ratio of aldehydes to alcohols produced in the process (some alcohol may be formed in small amounts along with the aldehyde which is normally the desired product) as well as the ratio of the normal to the branched-chain aldehyde derivative of the parent feedstock. The operating parameters contemplated by the present process are broadly the same as those conventionally employed in hydroformylation processes using rhodium complexes as already known in the art. For the sake of conveninece, these parameters will be generally set forth hereinbelow; it being understood, however, that the process parameters are not critical to achieving the improved results of the present invention as compared with processes using the prior-art ligands and do not, per se, form a part of it. That is, the present improvement lies in the use of the present improved ligands and not in the concomitant employment of any change from existing rhodium hydroformylation technology as already known to the art. To repeat the point, using the present improved catalyst system does not necessitate any departure from rhodium-catalyzed hydroformylations as already known, except for changing the ligand.

In general, the hydroformylation process is conducted under a total reaction pressure of hydrogen and carbon monoxide combined of one atmosphere or even less, up to a combined pressure of about 700 atmospheres abolute. Higher pressures can be employed but are normally not required. For economic reasons, however, pressures significantly greater than about 400 atmospheres absolute will not normally be employed.

The reaction is normally conducted at a temperature of from about 50° to about 200° C., with a temperature within the range of about 75° C. to about 150° C. being most commonly employed.

The ratio of partial pressures of hydrogen to carbon monoxide in the reaction vessel may be from about 10:1 to about 1:10 in accordance with the prior art, although it has been discovered that when using the present ligands this range may even be extended to about 50:1 to 1:50. Normally, however, the range of hydrogen partial pressure to that of carbon monoxide will be from about 6:1 to about 1:1, with a hydrogen:carbon monoxide ratio of about 1:1 usually being employed.

As is also known from the prior art, a liquid reaction medium is employed. Frequently this can comprise the ethylenically-unsaturated feedstock itself when it is liquid under the conditions existing in the reaction zone. A separately-added solvent can be employed if desired, however, particularly when the feedstock is of high volatility such that maintaining a liquid phase would require maintenance of excessive pressure under the reaction temperature which is to be employed. When the solvent is to be liquid other than the olefinic reactant or a product of the hydroformylation process (high-boiling reaction by-products are known to be useful for the purpose), it is preferred that it be one which is inert toward the catalyst and reactants under conditions obtaining within the reaction zone. Suitable reaction solvents include: benzene, toluene, diphenyl ether alone or mixed with biphenyl, esters, polypropylene oxides, ketones, aldehydes, ethylene glycol, alkanes, alcohols, and lactones.

Whatever may be the composition of the liquid reaction medium (i.e., whether it comprises predominantly a separate reaction solvent or a reaction feedstock or reaction product or by-product), the catalyst complex should be maintained in it at a concentration of about 0.1 to 50 millimoles/l calculated as rhodium. More preferably, about 0.5 to 20.0 millimoles/l of rhodium is recommended. While the catalyst can be formed ex-situ, it is conveniently prepared in-situ in the liquid reaction medium by introducing the ligand along with a suitable rhodium source and then allowing complexation to occur under the temperature to be employed in the hydroformylation reaction and in the presence of the hydrogen:carbon monoxide gas mixture which is to be used in the hydroformylation process. A suitable rhodium source is $HRh(CO)P\phi_3)_3$. Other rhodium sources which can be used include: rhodium on carbon, $Rh_2O_3$, $Rh(NO_3)_3$, $Rh_2(SO_4)_3$, $RhCl_3\cdot 3H_2O$, $RhClCO(P\phi_3)_2$, $[Rh(CO)_2Cl]_2[Rh(2,5-cyclooctadiene)Cl]_2$, $RhBr_3$, and $RhI_3$. If a halogen-containing rhodium source is to be employed, it is desirable to include with it a sufficient quantity of an alkaline reactant (e.g., sodium hydroxide) to scavenge the halide moiety out of the system as the complex is formed.

The following examples are given to further illustrate the practice of the invention. It will be understood that many variations can be made therefrom in accordance with the explanations given hereinabove.

EXAMPLE 1

(Run 24861-36)

As an initial step in preparing 1,1'-bis[bis(4-trifluoromethylphenyl) phosphino]ferrocene (hereinafter PTFL), 1,1'-dilithio ferrocene was prepared as follows:

A reactor was employed which comprised a 1-liter 3-neck flask equipped with a mechanical stirrer, reflex condenser, dropping funnel, and a connection for introducing nitrogen. Into the flask there was first introduced nitrogen. Into the flask there was first introduced 0.02339 mole of ferrocene and 300 ml of hexane. Next, 0.047 mole of n-butyl lithium (as a 2.4 M solution in hexane) was mixed in the dropping funnel with 0.047 mole of tetramethylethylenediamine, and the resulting adduct dissolved in hexane was added dropwise to the flask over a period of about 15 minutes. The reaction mixture was allowed to stand, with stirring, overnight under a nitrogen atmosphere.

EXAMPLE 2

(Run 24861-3,4)

In a two-liter three-neck flask equipped with a condenser, dropping funnel, stirrer, and nitrogen purge connection as in Example 1 above there were placed 1.056 moles of pyridine and 0.176 mole of diethylaminodichlorophosphine in about 400 ml of anhydrous diethyl ether. The contents of the flask were then cooled to between $-5°$ and $-10°$ using an ice-water-salt bath. Next, over a period of 45 minutes there was added 0.44 mole of para-trifluoromethylphenylmagnesium bromide. The contents of the flask were then allowed to warm up to room temperature and the resulting light brown-colored slurry was stirred overnight. The slurry was then filtered to recover the desired product, which has a reddish brown filtrate the solids on the filter were also washed three times with diethyl ether, the washings being combined with the filtrate.

EXAMPLE 3

(Run 24861-4)

The reddish brown filtrate from the preceding example was placed in a one-liter three-neck round-bottom flask equipped with a condenser, stirrer, and sparger. Gaseous HCl was then added through the sparger at a very slow rate. Immediately a white precipitate started to form while the color of the solution changed from reddish brown to orange. With continuing addition of HCl, a thick yellow slurry formed in the flask. As further quantities of HCl gas were added, the solids began to disappear, finally leaving in the flask a two-phase liquid which was yellow in color. Upon the evaporation of some of the liquid (diethyl ether) a white solid began to separate. This was filtered out and washed with dry anhydrous ether. The filtrate and washings were combined and the ether was separated from the resulting mixture by evaporation. After this the remaining liquid residue was subjected to vacuum distillation, the resulting distillate (collected at 110° C. and 0.4 mmHgA) was examined by nuclear magnetic resonance methods and confirmed to be pure bis(para-trifluoromethylphenyl)-phosphinous chloride. The yield was 39.1 grams.

EXAMPLE 4

(Run 24861-5)

The following describes the preparation of 1,1'-bis[di(para-trifluoromethylphenyl)phosphino]ferrocene using intermediates as prepared in the preceding examples.

In a 500 ml three-neck round-bottom flask equipped with a condenser, dropping funnel, and mechanical stirrer and having means for maintaining a nitrogen atmosphere therein, there were dissolved 29.8 millimoles of purified sublimed ferrocene in 250 ml of n-hexane. In the dropping funnel 60 millimoles of tetramethylethylenediamine were mixed with 60 millimoles of n-butyl lithium (as a solution of approximately 2M in hexane) to form an adduct of these two compounds. The adduct was then added from the dropping funnel into the ferrocene solution in the flask slowly, with stirring and while purging the flask with nitrogen. The resulting mixture was then allowed to stir overnight at ambient temperature and at atmospheric pressure.

After standing overnight, the lithiated ferrocene solution which had now been formed in the reaction flask and which was of an orange color was then cooled to about −5° to −10° C. using a water-ice-sodium chloride bath. Next, 59.6 millimoles of bis(para-trifluoromethylphenyl)phosphinous chloride was added dropwise to the flask. After this addition was completed the resulting mixture was allowed to warm up to room temperature while being continuously stirred, forming in the flask a dark brown colored homogeneous solution. To this solution there was then added 30 ml of methanol to decompose any unreacted n-butyl lithium, after which the contents of the flask were extracted three times with 300 ml of water at each extraction.

The organic layer from the extraction was then placed in a 1000 ml flask and all the liquid was evaporated therefrom. The resulting solids were then washed twice with n-hexane, using about 200 ml each time. This was followed with a diethyl ether wash. The resulting washed solids product was then dried in a vacuum. The ether washings were also evaporated and the resulting solids were likewise dried. The hexane washings were evaporated and dried in the same way. The primary solids product obtained from evaporating the organic layer from the extraction amounted to 1.8 grams and had a melting point range of 153° to 156° C. By proton magnetic resonance examination, this material was at least 95% pure 1,1'-bis[di(para-trifluoromethylphenyl)phosphino]ferrocene. The solids obtained from the evaporation of the ether washings amounted to 1.7 grams and melted at 127° to 155° C., while the solids obtained by evaporation of the hexane washings amounted to 10.0 grams and melted at 130 to 145° C. The 1.8 grams melting at 153°-156° C. were used as the "PTFL" liquid in those of the runs described below in which this was the ligand employed.

In the examples which are to follow, use is made of certain abbreviations to designate the ligands which were employed in the several hydroformylation runs described therein. These are tabulated below, the abbreviation being listed first, followed then by a brief chemical name and, finally, the complete chemical name. Of these the PCFL, the MFFL, and the PTFL are improved ligands within the ambit of the present invention:

FL:ferrocene ligand:1,1'-bis(diphenylphosphino)ferrocene

PMFL:p-methoxy ferrocene ligand:1,1'[ i(4-methoxyphenyl)phosphino] ferrocene

PCFL:p-chloro ferrocene ligand:1,1'-bis[di(4-chlorophenyl)phosphino] ferrocene

MFFL:m-fluoro ferrocene ligand:1,1'-bis[di(3-fluorophenyl)phosphino] ferrocene

PTFL:p-trifluoromethyl ferrocene ligand:1,1'-bis[di(4-trifluoromethylphenyl)phosphino] ferrocene DTFL:di-m-trifluoromethyl ferrocene ligand: 1,1'-bis(bis[3,5-bis(trifluoromethyl)phenyl]phosphino) ferrocene Unless otherwise indicated, the operating procedure which was employed in each of the examples which are to follow hereinbelow was as follows.

A 300 ml stirred stainless steel autoclave was charged with toluene as inert reaction solvent, typically 60 ml, along with rhodium, normally as HRh(CO)(P$\phi_3$)$_3$ in an amount to obtain the desired molar concentration of rhodium as indicated in the tables. Also charged to the reactor was the desired amount of the indicated ligand, in an amount sufficient to obtain the indicated ligand concentration. In certain cases the ligand was known to be impure, but this was compensated for by always adding sufficient ligand that the molar ratio of pure ligand to rhodium would be in all cases at least 1.5:1. The autoclave was then closed and flushed several times with synthesis gas, which was a 1:1 mixture of hydrogen and carbon monoxide. The autoclave was then pressured to the indicated 1:1 hydrogen:CO synthesis gas pressure after which its temperature was adjusted to the indicated reaction temperature of about 110° C. Next, 1-hexane, which had been preheated to the reaction temperature, was pressured into the autoclave from a reservoir which was pressured by the 1:1 synthesis gas. Unless otherwise indicated, 20 ml of the 1-hexane was used. It is to be noted that hexane was used throughout these runs for the reason that it is comparatively easy to handle under laboratory conditions. Other olefinic feedstocks such as propylene can be used, as explained hereinabove.

Additional synthesis gas was then admitted into the autoclave from an external reservoir (which was maintained continuously at a pressure higher than that of the autoclave) so as to attain and subsequently maintain, in the autoclave the desired indicated reaction pressure.

Upon attainment of the desired autoclave reaction pressure, the run was taken as having been started, and thereafter the progress of the reaction was monitored by continuously observing the rate at which the pressure in the external synthesis gas reservoir declined as the gas contained was consumed in the reaction autoclave. When the rate of reaction had dropped to an extremely low level, as indicated by a very low rate of decline of the synthesis gas reservoir pressure, the autoclave was cooled to ambient temperature and its contents were removed and analyzed chromatographically.

EXAMPLE 5

The following are the results obtained when hydroformylating 1-hexene by the procedure outlined immediately above, using a variety of ligands as shown. The run using PMFL ligand illustrates that this ligand, which has a negative Hammett's sigma value, gives less satisfactory results than obtained with the FL ligand which has a sigma value of 0.0. The remaining three tabulated runs show increasingly beneficial results, as measured by the normal:iso ratio in the aldehyde products, as the sigma value of the substituent is increased from 0.227 to 0.540. The ligands which were employed in these runs were not all of high purity, but sufficient excess of ligand was used in each case that it was certain that the ratio of contained pure ligand moiety to rhodium was at least 1.5:1.

e.g., up to about 15:1 in many instances. The higher ratios are actually to be preferred in an industrial installation. For example, increasing the hydrogen:carbon monoxide ratio from 1:1 up to 4:1, by leaving the carbon monoxide partial pressure unchanged while increasing the hydrogen partial pressure to obtain the desired ratio, increases the ratio of normal aldehyde to iso-aldehyde

TABLE I
Rh CATALYZED HYDROFORMYLATION OF 1-HEXENE, 50 psig

| Run No.[a] | 24844–42 | 22959–46[c] | 24844–26* | 23054–35 | 24844–36 | 24844–49 |
|---|---|---|---|---|---|---|
| Rh conc., mM | 0.625 | 2.5 | 0.625 | 1.25 | 1.25 | 1.25 |
| Ligand | PMFL | FL | PCFL | MFFL | PTFL | DTFL |
| Conc., mM[b] | 3.75 | 5.0 | 3.75 | 3.41 | 3.75 | 3.75 |
| Temp., °C. | 110 ± 0.5 | 110 ± 0.5 | 110 ± 1 | 109 ± 1 | 110 ± 1 | 110 ± 1 |
| Pres. of 1:1 $H_2$:CO, psig | 52 ± 2 | 50 ± 1 | 52 ± 2 | 51 ± 2 | 51 ± 1 | 50 ± 2 |
| n/iso ratio | 5.37 | 6.19 | 8.64 | 10.1 | 13.7 | 11.6 |
| % Ald, which is n | 84.3 | 86.1 | 89.6 | 91.0 | 93.2 | 92.1 |
| Conv., % | 98.2 | 99.8 | 99.6 | 99.4 | ~100 | 99.6 |
| $K_{obs}$/mM Rh, min$^{-1}$ | 0.018 | 0.047 | 0.060 | 0.028 | 0.111 | 0.038 |
| Eff. to prod., % | | | | | | |
| Heptanal | 81.6 | 84.3 | 81.2 | 81.9 | 79.8 | 81.6 |
| 2-Methylhexanal | 15.2 | 13.7 | 9.4 | 8.1 | 5.8 | 15.2 |
| 2-Hexene | 2.7 | 0.7 | 8.3 | 8.9 | 13.1 | 2.7 |
| Hexane | 0.5 | 1.3 | 1.1 | 1.1 | 1.3 | 0.5 |
| σ Value of substituent[d] | −0.268 | 0.0 | 0.227 | 0.337 | 0.540 | 0.430 |

[a]Except for the "*" run, 60 cc of toluene and 20 cc of 1-hexene were used. In the "*" run these amounts were halved.
[b]Since some of the ligands were impure, enough ligand was used to insure ligand/Rh ratios of at least 1.5:1 in all cases.
[c]In this run Rh(CO)(FL)Cl was used as the source of Rh and ½ of the FL·NaOH was added to the reaction mixture to remove Cl. All other runs used HRhCO(Pφ$_3$)$_3$ as the Rh source.
[d]Hammett's sigma value as previously explained.

The preceding Table I presents the results of hydroformylation reactions carried out at a pressure of 50 psig. The following Table II presents results obtained with the same ligand but operating at 100 psig. It will be noted here again that the PTFL ligand, which has the highest sigma value of the ligands tested, gave the most attractive results as measured by normal:iso ratio in the aldehyde product.

in the hydroformylation product. This effect is demonstrated in Table III which is set forth hereinbelow, which indicated a levelling off of the effect at about 3:1.

With regard to the variations in the synthesis gas pressure to be maintained in the hydroformylation reaction zone, it has been observed that the ratio of normal aldehyde to iso-aldehyde in the product tends to decrease with increasing pressure when the partial pres-

TABLE II
Rh CATALYZED HYDROFORMYLATION OF 1-HEXENE, 100 psig

| Run No.[a] | 24844–28 | 22959–43[c] | 24844–4* | 24885–31 | 24844–35 | 24917–1 |
|---|---|---|---|---|---|---|
| Rh conc., mM | 0.625 | 2.50 | 1.25 | 1.25 | 1.25 | 1.25 |
| Ligand | PMFL | FL | PCFL | MFFL | PTFL | DTFL |
| Conc., mM[b] | 3.75 | 5.0 | 7.50 | 2.50 | 3.75 | 3.75 |
| Temp., °C. | 110 ± 1 | 110 ± 1 | 110 ± 0.5 | 110 ± 1 | 110 ± 1 | 110 ± 1 |
| Pres. of 1:1 $H_2$:CO, psig | 102 ± 3 | 101 ± 1 | 101 ± 2 | 100 ± 2 | 100 ± 1 | 100 ± 2 |
| n/iso ratio | 4.77 | 5.59 | 6.65 | 8.15 | 12.4 | 11.9 |
| % Ald, which is n | 82.7 | 84.8 | 86.9 | 89.1 | 92.6 | 92.2 |
| Conv., % | 99.4 | 99.8 | 99.9 | ~100 | 99.9 | 99.2 |
| $K_{obs}$/mM Rh;min | 0.028 | 0.027 | 0.042 | | 0.091 | 0.030 |
| Eff. to prod., % | | | | | | |
| Heptanal | 80.5 | 83.8 | 81.3 | 83.0 | 86.4 | 81.5 |
| 2-methylhexanal | 16.8 | 15.0 | 12.2 | 10.2 | 7.0 | 6.8 |
| 2-Hexene | 2.2 | 0.6 | 5.8 | 6.0 | 5.9 | 10.7 |
| Hexane | 0.5 | 0.6 | 0.7 | 0.8 | 0.7 | 0.9 |
| σ Value of substituent[d] | −0.268 | 0.0 | 0.227 | 0.337 | 0.540 | 0.430 |

[a]Except for the "*" run, 60 cc of toluene and 20 cc of 1-hexene were used. In the "*" run these amounts were halved.
[b]Since some of the ligands were impure enough ligand was used to insure ligand/Rh ratios of at least 1.5:1 in all cases.
[c]In this run Rh(CO)(FL)Cl was used as the source of Rh and ½ of the FL·NaOH was added to the reaction mixture to remove Cl. All other runs used HRhCO(Pφ$_3$)$_3$ as the Rh source.
[d]Hammett's sigma value as previously explained.

The synthesis gas used in the runs tabulated above was a 1:1 mixture of hydrogen and carbon monoxide. This mixture was chosen (a) because it was a convenient basis for comparison of the several ligands etc., and (b) because the net input of synthesis gas into an operating hydroformylation system is normally about 50% hydrogen and 50% carbon monoxide. As previously explained, however, other synthesis gas compositions can be employed if desired and, in a continuously operating hydroformylation reaction system with recycles, the gas actually circulating through the reaction zone may have a higher ratio of hydrogen to carbon monoxide, sure of 1:1 synthesis gas is much above the range of about 50 to 100 psi, so that the partial pressure of 1:1 synthesis gas need not be much above about 50 to 100 psi (equivalent to a carbon monoxide partial pressure of about 25 to 50 psi). Increasing the hydrogen partial pressure, while leaving that of the carbon monoxide unchanged, has beneficial results as explained above. In converting hexene to heptanal (i.e., when hydroformylating 1-hexene), the efficiency of conversion of the hexene to the desired heptanal with a 1:1 synthesis gas is slightly greater at 70 psi partial pressure of the 1:1 synthesis gas than at about 50 psi. At about 40 psi and below, the efficiency to heptanal begins to decline. Thus, a partial pressure of 1:1 synthesis gas of about 50 to 100 psi is normally preferred. In connection with these comments regarding pressures, it should be noted that the several runs which are presented herein express pressure in terms of psig, which is what was actually measured. This includes, of course, the pressure exerted by liquids such as the hexene, which amounts to about 1 atmosphere.

EXAMPLE 6

The following illustrates the effect of hydrogen:carbon monoxide ratio in runs which are otherwise carried out under the same conditions as employed in Example 5.

TABLE III
Rh CATALYZED HYDROFORMYLATION OF 1-HEXENE WITH PTFL LIGAND AT VARYING H$_2$:CO RATIO

| Run No. | 24844-36 | 24885-39 | 24885-40 | 14917-14 | 24885-41 | 14917-17 | 24885-42 | 24917-15 |
|---|---|---|---|---|---|---|---|---|
| Rh amt., mmoles | 0.10 | 0.05 | 0.05 | 0.05 | 0.05 | 0.05 | 0.05 | 0.05 |
| PTFL amt.,mmoles | 0.30 | 0.15 | 0.15 | 0.15 | 0.15 | 0.15 | 0.15 | 0.15 |
| PTFL/Rh ratio | 3.0 | 3.0 | 3.0 | 3.0 | 3.0 | 3.0 | 3.0 | 3.0 |
| Temp., °C. | 110.5 ± 1.5 | 110.5 ± 0.5 | 110 ± 1 | 110 ± 1 | 110 ± 1 | 110 ± 1 | 110.5 ± 1.5 | 110 ± 1 |
| Pres., psig | 50 ± 2 | 75 ± 2 | 101 ± 2 | 101 ± 2 | 126 ± 2 | 125 ± 2 | 176 ± 2 | 175 ± 2 |
| H$_2$:CO ratio | 1:1 | 2:1 | 3:1 | 3:1 | 4:1 | 4:1 | 6:1 | 6:1 |
| CO, psig | 25 | 25 | 25 | 25 | 25 | 25 | 25 | 25 |
| n/iso ald. ratio | 13.7 | 17.1 | 21.7 | 20.3 | 19.1 | 22.7 | 21.8 | 21.8 |
| % ald. that is n | 93.2 | 94.5 | 95.6 | 95.3 | 95.0 | 95.8 | 95.6 | 95.6 |
| Conv, % | 99.9 | 99.9 | 99.9 | 99.9 | 99.9 | 99.9 | 99.9 | 99.9 |
| K$_{obs}$,min$^{-1}$ | 0.138 | 0.124 | 0.149 | 0.154 | 0.143 | 0.143 | 0.169 | 0.151 |
| K$_{obs}$/mM Rh | 0.111 | 0.198 | 0.238 | 0.247 | 0.228 | 0.229 | 0.270 | 0.241 |
| Eff. to prod., % | | | | | | | | |
| Heptanal | 79.8 | 81.4 | 84.4 | 84.6 | 81.7 | 84.5 | 83.4 | 84.5 |
| 2-Mehexanal | 5.8 | 4.7 | 3.9 | 4.2 | 4.3 | 3.7 | 3.8 | 3.9 |
| 2-Hexene | 13.1 | 11.6 | 9.3 | 8.7 | 10.0 | 8.7 | 8.5 | 7.6 |
| Hexane | 1.3 | 2.3 | 2.4 | 2.5 | 4.0 | 3.1 | 4.3 | 4.0 |

When, as in the foregoing examples, the hydroformylation reaction product is heptanal or other like aldehyde which is a liquid under the pressure and temperature conditions obtaining within the reaction zone, the product aldehyde is recovered from the liquid reaction medium by distillation of the liquid reaction medium in a separate step or steps which are known to the art and which are outside the scope of the present invention. Also, it is feasible and desirable in these cases to conduct the hydroformylation reaction under conditions such that, as demonstrated in the preceding examples, there is a high conversion of the olefinic feedstock so as to minimize processing complications inherent in separating a reaction product which contains a substantial fraction of unconverted feedstock. For example, when the feedstock is an alkene having more than three carbon atoms, some migration of the terminal double bond is experienced such that a relatively inert internally-unsaturated alkene builds in the reaction system whereby any recycled olefin would contain increasing proportions of this material.

However, when hydroformylating alkenes such as ethylene and propylene which are not liquid under the hydroformylation reaction conditions and which (specifically in the case of ethylene and propylene) do not have the problem of internal migration of the double bond, the reaction is carried out, as also known in the art, in a manner which, as regards olefin conversion and the mode of aldehyde product recovery, differs from the techniques employed with higher olefinic feedstocks such as hexene. Specifically, the gaseous olefin feedstock is circulated, as by sparging, through the liquid reaction medium rather than being admixed thereinto as a liquid. A mixture of unreacted olefin synthesis gas, and aldehyde product is continuously withdrawn from the reaction zone in the vapor phase, and the aldehyde product is separated therefrom by condensation. The unreacted gas mixture is then recycled back to the reaction zone, typically after withdrawing a slipstream therefrom for the purpose of preventing buildup of inert contaminants. It will be understood, of course, that the recycling gas stream is continuously monitored and that carbon monoxide, hydrogen, and olefin are continuously injected into it so as to maintain the desired proportions of these components in the gas being sparged into the liquid reaction medium.

In hydroformylating either ethylene or propylene, it is recommended that the reaction zone be maintained at a temperature of about 80° to 120° C. and that the mixture of olefinic feedstock and synthesis gas being sparged therethrough comprise about 10 to 40% olefin, 5 to 30% carbon monoxide, and 40 to 70% hydrogen with the total pressure being approximately 5 to 30 atmospheres absolute. The liquid reaction medium should contain about 0.01 to 1.0% rhodium. The reaction medium can be, as previously explained, a separately-added inert liquid such as diphenyl ether, xylene, toluene, or polypropylene oxide. Alternatively it can be a mixture of high-boiling by-products of the hydroformylation reaction as already known in the art.

In hydroformylating 1-octene to produce nonanal, which, like the heptene formed by hydroformylating 1-hexene, can be oxidized to form the industrially-useful corresponding alkanoic acid, the recommended processing parameters are the same as when hydroformylating 1-hexene.

The embodiments of the invention in which an exclusive property or privilege is claimed are defined as follows:

1. 1,1'Bis[di(4-chlorophenyl)phosphino]ferrocene.
2. 1,1'-Bis[di(3-fluorophenyl)phosphino]ferrocene.
3. 1,1'-Bis[di(4-trifluoromethylphenyl)phosphino]ferrocene.

* * * * *

UNITED STATES PATENT AND TRADEMARK OFFICE
CERTIFICATE OF CORRECTION

PATENT NO. : 4,152,344
DATED : May 1, 1979
INVENTOR(S) : Jerry D. Unruh

It is certified that error appears in the above-identified patent and that said Letters Patent are hereby corrected as shown below:

In column 12, line 3, for "1,1' [ i(4-methox" read -- 1,1'bis[di(4-methox --.

In column 12, line 34, for "hexane", read -- hexene --.

In column 12, line 36, for "1-hexane", read -- 1-hexene --.

In column 12, line 36, for "hexane", read -- hexene --.

Signed and Sealed this

Eighteenth Day of December 1979

[SEAL]

Attest:

SIDNEY A. DIAMOND

Attesting Officer     Commissioner of Patents and Trademarks